United States Patent [19]

Cooper et al.

[11] Patent Number: 4,771,058
[45] Date of Patent: Sep. 13, 1988

[54] 3,4-DIAMINO-1,2,5-THIADIAZOLE-1-OXIDES HAVING HISTAMINE $H_1$-ANTAGONIST ACTIVITY

[75] Inventors: David G. Cooper, Letchworth; George S. Sach, Welwyn, both of England

[73] Assignee: Smith Kline & French Laboratories Limited, Welwyn Garden City, England

[21] Appl. No.: 873,009

[22] Filed: Jun. 11, 1986

[30] Foreign Application Priority Data

Jun. 13, 1985 [GB] United Kingdom ............... 8514977
Jun. 29, 1985 [GB] United Kingdom ............... 8516554

[51] Int. Cl.$^4$ .................... C07D 417/12; A61K 31/44
[52] U.S. Cl. .................... 514/342; 514/338; 514/333; 514/256; 546/277; 546/270; 546/256; 544/333
[58] Field of Search ............. 546/277, 270, 256; 544/333; 514/342, 338, 333, 256

[56] References Cited

U.S. PATENT DOCUMENTS

| | | | |
|---|---|---|---|
| 4,374,248 | 2/1983 | Crenshaw et al. | 548/134 |
| 4,444,772 | 4/1984 | Sach | 544/320 |
| 4,471,122 | 9/1984 | Crenshaw et al. | 546/209 |
| 4,486,434 | 12/1984 | Sach | 544/320 |
| 4,532,246 | 7/1985 | Ife | 514/275 |
| 4,532,252 | 7/1985 | Sach | 514/357 |
| 4,537,890 | 8/1985 | Sach | 544/320 |
| 4,537,891 | 8/1985 | Sach | 514/272 |
| 4,547,506 | 10/1985 | Ife | 514/272 |
| 4,548,940 | 10/1985 | Ife | 514/272 |
| 4,692,456 | 9/1987 | Ife | 546/277 |

FOREIGN PATENT DOCUMENTS

0040696-A 12/1981 European Pat. Off. .

Primary Examiner—Jane T. Fan
Attorney, Agent, or Firm—Linda E. Hall; Janice E. Williams; Alan D. Lourie

[57] ABSTRACT

The invention relates to a class of 3,4-diamino-1,2,5-thiadiazole-1-oxides which have histamine $H_1$-antagonist activity. A preferred compound of the invention is 3-[3-(5-bromo-3-methylpyrid-2-ylamino)-propylamino]-4-amino-1,2,5-thiadiazole-1-oxide.

27 Claims, No Drawings

3,4-DIAMINO-1,2,5-THIADIAZOLE-1-OXIDES HAVING HISTAMINE H₁-ANTAGONIST ACTIVITY

This invention relates to certain pyridine derivatives, a process for their preparation, compositions containing them and their use as histamine H₁-antagonists.

Histamine, a physiologically active compound endogenous in mammals, exerts its action by interacting with certain sites called receptors. One type of receptor is known as a histamine H₁-receptor (Ash and Schild, Brit. J. Pharmac. 1966, 27, 427) and the actions of histamine at these receptors are inhibited by drugs commonly called "antihistamines" (histamine H₁-antagonists) a common example of which is mepyramine. A second type of histamine receptor is known as the H₂-receptor (Black et al Nature 1972, 236, 385). The actions of histamine at these receptors are not inhibited by mepyramine but are inhibited by burimamide. Compounds which inhibit the actions of histamine at histamine H₂-receptors are called histamine H₂-antagonists.

Histamine H₁-antagonists are useful in the treatment of diseases for example, bronchial asthma, rhinitis, hayfever and allergic eczema, whose symptoms are mediated by the effects of histamine at H₁-receptors.

European Patent Application No. 0112707 discloses and claims "compounds of formula (1):

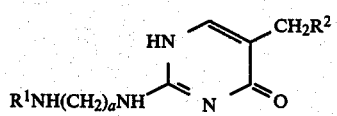

and pharmaceutically acceptable acid addition salts thereof where $R^1$ is 2- or 3-pyridyl optionally bearing one or two substituents which are the same or different and which are $C_{1-4}$alkyl, $C_{1-4}$alkoxy, halogen, nitro, cyano or trifluoromethyl;

a is 2 to 4; and $R^2$ is phenyl optionally bearing one or two substituents which are the same or different and are halogen, hydroxy, $C_{1-4}$alkyl or $C_{1-4}$alkoxy or a methylenedioxy group or is 3-pyridyl; N-oxo-3-pyridyl; 6-methyl-3-pyridyl; N-oxo-6-methyl-3-pyridyl; 6-hydroxymethyl-3-pyridyl; 4,6-dimethyl-3-pyridyl; N-oxo-4,6-dimethyl-3-pyridyl; 6-hydroxymethyl-4-methyl-3-pyridyl; 5,6-dimethyl-3-pyridyl; N-oxo-5,6-dimethyl-3-pyridyl; 6-hydroxy-methyl-5-methyl-3-pyridyl; 4-pyridyl or N-oxo-4-pyridyl."

These compounds are described as histamine H₁-antagonists.

European Patent Application No. 0112142 discloses and claims "compounds of formula (1):

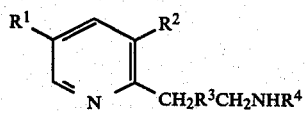

and pharmaceutically acceptable salts thereof; where $R^1$ is halogen, nitro, amino (or a pharmaceutically acceptable derivative of the amino group which is convertible in vivo into amino) or $C_{1-4}$alkyl;

$R^2$ is halogen, nitro, amino (or a pharmaceutically acceptable derivative of the amino group which is convertible in vivo into amino), $C_{1-4}$alkyl, or $C_{3-4}$alkoxy;

$R^3$ is a $C_{1-3}$alkylene group; and $R^4$ is inter alia a group of formula (5):

where n is 0, 1 or 2 and is $R^{10}$ is hydrogen, $C_{1-6}$alkyl, or optionally substituted phenyl or phenyl($C_{1-6}$)alkyl (the substituents being one or more $C_{1-6}$alkyl, or $C_{1-6}$alkoxy groups or halogen atoms); or a methylenedioxy group or optionally substituted pyridyl or pyridyl ($C_{1-6}$)alkyl where the optional substituents are one or more $C_{1-6}$alkyl or $C_{1-6}$alkoxy groups or halogen atoms; or $R^4$ is a group of formula (6):

where $R^{11}$ is hydrogen, $C_{1-6}$alkyl, optionally substituted phenyl or phenyl($C_{1-6}$)alkyl, (the substituents being one or more $C_{1-6}$alkyl or $C_{1-6}$-alkoxy groups or halogen atoms or a methylenedioxy group); optionally substituted pyridyl or pyridyl ($C_{1-6}$)alkyl, the optional substituents being one or more $C_{1-6}$alkyl groups or $C_{1-6}$alkoxy groups or halogen atoms; or a group of formula (7):

where $R^{12}$ is hydrogen or $C_{1-6}$alkyl, $R^{15}$ is hydrogen or together with $R^{12}$ a fused benzene ring and m is 0, 1 or 2 or a group of formula (8):

where $R^{12}$ is hydrogen or $C_{1-6}$alkyl."

These compounds are also described as histamine H₁-antagonists.

According to the present invention there are provided compounds of formula (1) :

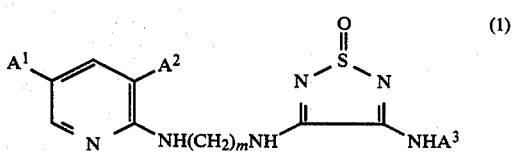

and pharmaceutically acceptable salts thereof; where $A^1$ is halogen, nitro, amino, $C_{1-6}$alkyl or $C_{3-4}$alkoxy;

$A^2$ is hydrogen, halogen, nitro, amino, $C_{1-6}$alkyl or $C_{3-4}$alkoxy;

m is 3 or 4;

$A^3$ is hydrogen, $C_{1-6}$alkyl or $CH_2A^4$ where $A^4$ is phenyl optionally bearing one or two substituents which are the same or different and are $C_{1-6}$alkyl, $C_{1-6}$alkoxy, halogen or hydroxy, or a methylenedioxy group;

or is pyridyl optionally bearing one or two substituents which are the same or different and are $C_{1-6}$alkyl, $C_{1-6}$alkoxy, halogen or hydroxy;

or is N-oxopyridyl optionally bearing a $C_{1-6}$alkyl, $C_{1-6}$alkoxy, or halogen substituent;

or is pyrimidinyl optionally bearing one or two $C_{1-6}$alkyl groups.

The compounds of this invention differ in structure from those described in European Patent Application No. 0112707 in that the pyrimidine group has been replaced by a thiadiazolyl group.

The compounds of this invention differ in structure from those in European Patent Application No. 0112142 in that the —$CH_2R^3CH_2$ group has been replaced by an —$NH(CH_2)_m$ group.

The compounds of this invention differ in activity from these known compounds because they have a relatively higher level of $H_1$-antagonist activity in vivo following oral administration as measured, for example, in the guinea pig bronchoconstriction assay described herein.

$A^1$ and $A^2$ can represent any one of the halogens, fluorine, chlorine, bromine or iodine.

Preferably $A^1$ is halogen, particularly bromine.

Examples of $C_{1-6}$alkyl groups for $A^1$ and $A^2$ are methyl, ethyl, n-propyl, iso-propyl, n-butyl and t-butyl.

Examples of $C_{3-4}$alkoxy groups for $A^1$ and $A^2$ are n-propoxy and n-butoxy.

Preferably $A^2$ is either $C_{1-6}$alkyl or amino and particularly is methyl.

Preferably m is 3.

Examples of $C_{1-6}$alkyl groups which $A^3$ represents and $C_{1-6}$alkyl substituents for $A^3$ and $A^4$ are methyl, ethyl and n-propyl.

Examples of $C_{1-6}$alkoxy substituents for $A^4$ are methoxy, ethoxy and n-propoxy.

Examples of halogen substituents for $A^4$ are fluorine, chlorine, bromine and iodine.

One class of compounds falling within the scope of this invention is where $A^3$ is $CH_2A^4$ and $A^4$ is phenyl optionally bearing one or two substituents which are the same or different and are $C_{1-6}$alkyl, $C_{1-6}$alkoxy, halogen or hydroxy or a methylenedioxy group.

A particular example of the group $CH_2A^4$ 4-fluorobenzyl.

A further class of compounds falling within the scope of this invention is where $A^4$ is pyridyl optionally bearing one or two substituents which are the same or different and are $C_{1-6}$alkyl, $C_{1-6}$alkoxy, halogen or hydroxy.

Examples of optionally substituted pyridyl groups for $A^4$ are optionally substituted pyrid-2-yl, pyrid-3-yl, or pyrid-4-yl groups, and particularly pyrid-3-yl, 6-methylpyrid-3-yl and 6-methoxypyrid-3-yl.

A particular example is pyrid-3-yl.

A further class of compounds within the scope of this invention is where $A^4$ is N-oxopyridyl optionally bearing a $C_{1-6}$alkyl, $C_{1-6}$alkoxy or halogen substituent.

Preferably the pyridyl group is a 3- or 4-pyridyl group.

Examples of particular values for $A^4$ in compounds of this class are 6-methyl-N-oxopyrid-3-yl, 6-methoxy-N-oxopyrid-3-yl, 6-chloro-N-oxopyrid-3-yl and especially N-oxopyrid-3-yl.

Preferably $A^4$ is 4-fluorophenyl, pyrid-3-yl, pyrimid-4-yl, N-oxopyrid-3-yl or N-oxo-pyrid-4-yl.

Particular compounds within the scope of this invention are:

3-[4-(5-bromo-3-methylpyrid-2-ylamino)butylamino]-4-amino-1,2,5-thiadiazole-1-oxide;

3-[3-(5-bromo-3-methylpyrid-2-ylamino)propylamino]-4-amino-1,2,5-thiadiazole-1-oxide;

3-[3-(5-bromo-3-methylpyrid-2-ylamino)propylamino]-4-methylamino-1,2,5-thiadiazole-1-oxide;

3-[3-(5-bromo-3-methylpyrid-2-ylamino)propylamino]-4-(4-fluorobenzylamino-1,2,5-thiadiazole-1-oxide;

3-[3-(5-bromo-3-methylpyrid-2-ylamino)propylamino]-4-pyrimid-4-ylmethylamino-1,2,5-thiadiazole-1-oxide;

3-[3-(5-chloro-3-methylpyrid-2-ylamino)propylamino]-4-amino-1,2,5-thiadiazole-1-oxide;

3-[3-(3,5-dibromopyrid-2-ylamino)propylamino]-4-amino-1,2,5-thiadiazole-1-oxide;

3-[3-(5-bromo-3-methylpyrid-2-ylamino)propylamino]-4-(pyrid-3-ylmethylamino)-1,2,5-thiadiazole-1-oxide;

3-[3-(5-bromo-3-methylpyrid-2-ylamino)propylamino]-4-(N-oxopyrid-3-ylmethylamino-1,2,5-thiadiazole-1-oxide;

3-[3-(5-bromopyrid-2-ylamino)propylamino]-4-amino-1,2,5-thiadiazole-1-oxide;

3-[3-(5-bromo-3-methylpyrid-2-ylamino)propylamino]-4-(N-oxopyrid-4-ylmethylamino)-1,2,5-thiadiazole-1oxide;

and their pharmaceutically acceptable salts.

Compounds of formula (1) form pharmaceutically acceptable salts with pharmaceutically acceptable salt-forming acids. Examples of pharmaceutically acceptable acid addition salts of compounds of formula (1) are those formed with hydrochloric, hydrobromic, sulphuric, phosphoric, acetic, citric, maleic, lactic, ascorbic, methanesulphonic, 2-hydroxyethanesulphonic, toluene-4-sulphonic, ethanedisulphonic, ethanesulphonic and camphorsulphonic acids.

Compounds of formula (1) can be prepared by reacting a compound of formula (2):

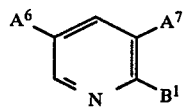
(2)

where $A^6$ is a group $A^1$ or a protected amino group and $A^7$ is a group $A^2$ or a protected amino group where $A^1$ and $A^2$ are as defined with reference to formula (1) and $B^1$ is a group —$NH(CH_2)_mNH_2$ where m is as defined with reference to formula (1) or is a group displaceable with amine, with a compound of formula (3):

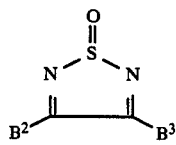
(3)

where $B^2$ is a group displaceable with amine when $B^1$ is —NH(CH$_2$)$_m$NH$_2$, where m is defined with reference to formula (1), or $B^2$ is —NH(CH$_2$)$_m$NH$_2$ when $B^1$ is a group displaceable with amine; and $B^3$ is a group displaceable with amine or a group NHA$^3$, and where $B^3$ is a group displaceable with amine, reacting the product so obtained with an amine of the formula (4):

$$A^3NH_2 \qquad (4)$$

where $A^3$ is as defined with reference to formula (1) and thereafter, where necessary, removing any protecting group from a protected amino group in the product so obtained; and optionally converting the compound of formula (1) so obtained into a salt.

In the compounds of formula (2) the protecting group in the protected amino group $A^6$ or $A^7$ can be any standard amino protecting group which is stable under the reaction conditions. For example it can be $C_{1-6}$-alkanoyl, benzyl or benzoyl. These protecting groups can be introduced and removed by standard methods.

The use of protecting groups is discussed in T. W. Greene, Protective Groups in Organic Synthesis, 1981, John Wiley & Sons, IBSN 0-471-05764-9.

Examples of leaving groups displaceable by amines are where $B^1$ is halogen especially bromine and where $B^2$ or $B^3$ are QS-, QSO-, QSO$^2$-, or QO (Q being $C_{1-6}$alkyl, aryl or aralkyl). Where $B^2$ or $B^3$ are QO-, Q is preferably methyl or phenyl. Preferably $B^2$ and $B^3$ are QO- where Q is methyl.

Compounds of formula (2) where $B^1$ is a group —NH(CH$_2$)$_m$NH$_2$ where m is as defined with reference to formula (1) can be prepared by reacting a compound of formula (2):

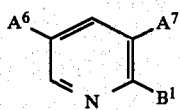
$$(2)$$

where $B^1$ is a group displaceable with amine, with an amine of formula (6):

$$NH_2(CH_2)_mNH_2 \qquad (6)$$

where m is as defined with reference to formula (1).

Compounds of formula (3) where $B^2$ is a group —NH(CH$_2$)$_m$NH$_2$ and $B^3$ is a group —NHA$^3$ can be prepared by reacting a compound of formula (3) where $B^2$ is a group displaceable with amine and $B^3$ is a group displaceable with amine or a group —NHA$^3$ with a compound of formula (6):

$$NH_2(CH_2)_mNH_2 \qquad (6)$$

and where $B^3$ is a group displaceable with amine reacting the product so obtained with a compound of formula (4) as previously defined.

It will be appreciated that each of the above mentioned reactions involves either the displacement of a displaceable group from a pyridine ring by an amine, or the displacement of a displaceable group from a thiadiazole ring by an amine. These reactions can be carried out under conditions well known in the art in respect of analogous displacement reactions, see, for example, No. EP 0112704-A. Thus when the reaction involves the displacement of a displaceable group from a pyridine ring, e.g. the reaction of a compound of the formula (2) wherein $B^1$ is a displaceable group, with a compound of the formula (6), it can be carried out at an elevated temperature in the absence of a solvent, for example at a temperature of from 80° C. to 170° C., preferably from 120° C. to 140° C., or in a solvent at an elevated temperature, for example the reflux temperature of the reaction mixture. When the reaction involves the displacement of a displaceable group from a thiadiazole ring, e.g. the reaction of a compound of the formula (2) wherein $B^1$ is a group NH(CH$_2$)$_m$NH$_2$ with a compound of the formula (3) wherein $B^2$ is a displaceable group, it can generally be carried out at moderate to low temperature, e.g. from 0° C. to room temperature. In the case of the displacement of a displaceable group $B^3$ by a group $A^3NH_2$, in certain instances, e.g. when $A^3$ is 4-pyridylmethyl or N-oxopyridylmethyl, the reaction can advantageously be conducted at more elevated temperatures, for example at reflux temperature when $A^3$ is N-oxopyridyl.

The choice of solvent is affected by the solubility characteristics of the reactants. Preferably the solvent is pyridine, a picoline or mixture of picolines, a $C_{1-6}$alkanol, 1,2-ethanediol, a high boiling alkoxyaryl ether, for example anisole, or a polar aprotic solvent, for example dimethylformamide, dimethylacetamide, dimethylsulphoxide, hexamethylphosphoramide, or sulpholane. When the reaction involves the displacement of a displaceable group from a thiadiazole ring, particularly preferably the solvent is a $C_{1-6}$alkanol, especially methanol and ethanol.

Compounds of formula (2) are known and can be made by analogy with known processes as described, for example, in European Patent Application No. 0112707.

Compounds of formula (3) are known or can be made by analogy with known processes as described, for example, in U.K. Patent Application No. 2067987A.

Compounds of formula (6) are known or can be made by analogy with known processes.

The histamine $H_1$-antagonist activity of the compounds of formula (1) can be demonstrated in vitro in the guinea pig ileum test. In this test an isolated portion of the guinea pig ileum is secured under tension (500 mg) between an anchorage and a transducer in a 10 ml tissue bath and immersed in magnesium free Tyrode solution with constant aeration at a temperature of 30° C. The output from the transducer is amplified. The amplified output is in turn fed to a flat bed recorder. Measured amounts of histamine are added to the tissue bath so that the histamine concentration increases stepwise until the force of the contraction reaches a maximum. The tissue bath is washed out and filled with fresh magnesium free Tyrode solution containing compound under test. The solution is left in contact with the tissue for 8 min. and measured amounts of histamine are added again until a maximum contraction is recorded. The assay is repeated with increasing concentrations of test compound and the dose of histamine giving 50% of maximum contraction is noted. A dose ratio (DR) was calculated by comparing the concentrations of histamine required to produce 50% maximum response in the absence and in the presence of the antagonist. A plot of Log DR-1 against Log D (the concentration of compound under test) is made and the point of intersection with the Log (DR-1) ordinate is taken as the measure of the activity (pA$_2$ value). All the compounds of the Examples below have pA$_2$ values of 8 or above.

The activity of compounds of formula (1) as histamine $H_1$-antagonists can be demonstrated in vivo by the inhibition of histamine induced bronchoconstriction. Guinea pigs of either sex are anaesthetised by intraperitoneal injection of sodium pentobarbitone, 90 mg/kg. The trachea is cannulated. The animal is respired artificially with a fixed volume of air just adequate to inflate the lungs. The pressure needed to inflate the lungs is monitored from the respiratory system using a low pressure transducer. Intravenous injection of histamine causes dose-dependent increases in the pressure to inflate the lungs reflecting the bronchoconstrictor action of histamine. Responses to histamine can be antagonised using histamine $H_1$-receptor antagonists.

Dose-response curves to histamine are established at 20, 40, 80, 160 and 320 nmols/kg. Antagonists are then administered by intravenous injection and 5 minutes later a new histamine dose-response curve is established increasing the doses of histamine as necessary. The effect of the antagonist can be quantified by the displacement, to the right, of the histamine dose-response curve, expressed as a dose-ratio. A series of doses of antagonists may be given to each animal allowing calculation of dose-ratios for each dose of antagonist.

For all the compounds exemplified below, the dose of compound required to give a dose ratio of 11 is in the range 0.033–1.1 $\mu$mole/kg, the majority of them requiring a dose of less than 0.4 $\mu$mole/kg.

In order to use the compounds of the invention as histamine $H_1$-antagonists, they can be formulated as pharmaceutical compositions in accordance with standard pharmaceutical procedure.

The invention also includes pharmaceutical compositions comprising a compound of formula (1) or a pharmaceutically acceptable salt thereof and a pharmaceutically acceptable carrier.

Compounds of formula (1) and their pharmaceutically acceptable salts can be administered topically or systemically.

Topical formulations for administration to the skin include lotions and creams. Topical formulations for administration to the respiratory tract include solutions for application via a nebulizer or as an aerosol, or a microfine insufflatable powder. The active ingredient in an insufflatable powder has a small particle size i.e. less than 50 microns and preferably less than 10 microns. The active material is co-presented with a solid carrier for example lactose which has a particle size of less than 50 microns.

Systemic administration can be achieved by rectal, oral or parenteral administration. A typical suppository formulation comprises the active compound with a binding agent and/or lubricating agent for example gelatine or cocoa butter or other low melting vegetable waxes or fats. Typical parenteral compositions consist of a solution or suspension of the active material in a sterile aqueous carrier or parenterally acceptable oil.

Compounds of formula (1) which are active when given orally can be formulated as syrups, tablets, capsules and lozenges. A syrup formulation generally consists of a suspension or solution of the compound in a liquid carrier for example ethanol, glycerine or water with a flavouring or colouring agent. Where the composition is in the form of a capsule, the solid in granular form optionally with a binding agent is encased in a gelatin shell. Where the composition is in the form of a tablet, any suitable pharmaceutical carrier routinely used for preparing solid formulations can be used. Examples of such carriers include magnesium stearate, starch, lactose, glucose, sucrose, and cellulose. Preferably the composition is in unit dose form for example a tablet, capsule or metered aerosol so that the patient may administer to himself a single dose.

Where appropriate, small amounts of bronchodilators and anti-asthmatics for example sympathomimetic amines particularly isoprenaline, isoetharine, salbutamol, phenylephrine and ephedrine; xanthine derivatives particularly theophylline and aminophylline; and corticosteroids particularly prednisolone and adrenal stimulants particularly ACTH can be included. As in common practice, the compositions will usually be accompanied by written or printed directions for use in the medical treatment concerned, in this case as a histamine $H_1$-antagonist for treatment of, for example, asthma, hayfever rhinitis or allergic eczema.

Each dosage unit for oral administration contains preferably from 5 to 200 mg of a compound of formula (1) or a pharmaceutically acceptable salt thereof calculated as the free base.

The pharmaceutical compositions of the invention will normally be administered to a man for the treatment of rhinitis, hayfever, bronchial asthma or allergic eczema. An adult patient will receive an oral dose of between 15 mg and 400 mg and preferably between 15 mg and 200 mg or an intravenous, subcutaneous or intramuscular dose of between 1 mg and 50 mg, and preferably between 1 mg and 10 mg of a compound of formula (1) or a pharmaceutically acceptable salt thereof calculated as the free base, the composition being administered 1 to 4 times per day.

The following Examples illustrate the invention.

EXAMPLE 1

3-(5-Bromo-3-methylpyrid-2-ylamino)propylamine (0.713 g) was added dropwise to a stirred solution of 3,4-dimethoxy-1,2,5-thiadiazole-1-oxide (0.639 g) in methanol (25 ml) at room temperature. After 4 hours at room temperature, methanolic ammonia (25 ml) was added at 0°–5° C. with stirring, the mixture allowed to stand overnight, then evaporated in vacuo. The residue was chromatographed on silica in 10% $CH_3OH/CHCl_3$. The product was crystallised from ethanol to give 4-amino-3-[3-(5-bromo-3-methylpyrid-2-ylamino)propylamino]-1,2,5-thiadiazole-1-oxide (0.322 g, 32%) m.p. 204°–205° C.

EXAMPLE 2

4-(5-Bromo-3-methylpyrid-2-ylamino)butylamine (0.7 g) in methanol was reacted with 3,4-dimethoxy-1,2,5-thiadiazole-1-oxide (0.44 g) overnight at room temperature. Methanolic ammonia (25 ml) was added and the reaction mixture was stirred for 2 hours. After evaporation, the residue was recrystallised from a mixture of acetonitrile and ether to yield 4-amino-3-[4-(5-bromo-3-methylpyrid-2-ylamino)-butylamino]-1,2,5-thiadiazole-1-oxide (0.45 g, 45%) m.p. 212°–214° C. dec.

EXAMPLE 3

Substituting 3-(5-chloro-3-methylpyrid-2-ylamino)-propylamine (1.10 g) for 3-(5-bromo-3-methylpyrid-2-yl-amino)propylamine, using corresponding molar proportions of reagents and conditions analogous to those described in Example 1 gave, after chromatography on silica, 10% $CH_3OH/CHCl_3$ and recrystallisation from propan-2-ol/methanol, 4-amino-3-[3-(5-chloro-3- methyl-pyrid-2-ylamino)propylamino]-1,2,5-thiadiazole-1-oxide (0.525 g, 30%), m.p. 200°–202° C.

EXAMPLE 4

Substituting 3-(3,5-dibromopyrid-2-ylamino)propylamine (0.84 g) for 3-(5-bromo-3-methylpyrid-2-ylamino)-propylamine, using corresponding molar proportions of reagents and conditions analogous to those described in Example 1 gave, after chromatography on silica in 10% CH₃OH/CHCl₃ and recrystallisation from propan-2-ol/methanol, 4-amino-3-[3-(3,5-dibromopyrid-2-ylamino) propylamino]-1,2,5-thiadiazole-1-oxide (0.18 g, 16%) m.p. 197°–203° C. (decomp.)

EXAMPLE 5

A solution of 3-(5-bromopyrid-2-ylamino)propylamine (1 g) and 3,4-dimethoxy-1,2,5-thiadiazole-1-oxide (0.71 g) was stirred in methanol for 3 hours. Methanol saturated with ammonia (10 ml) was added and the solution was stirred for 18 hours, concentrated in vacuo and the residue was chromatographed on silica eluted with 10% v:v methanol in chloroform followed by recrystallisation from methanol to give 3-[3-(5-bromo-pyrid-2-ylamino)propylamino]-4-amino-1,2,5-thiadiazole-1-oxide (0.63 g), m.p. 215°–216° C.

EXAMPLE 6

3-(5-Bromo-3-methylpyrid-2-ylamino)propylamine (1.0 g) was reacted with 3,4-dimethoxy-1,2,5-thiadiazole-1-oxide (0.65 g) in methanol for 6 hours. Methylamine in ethanol (15 ml) was added and stirred for 2 hours. After evaporation the residue was recrystallised from a mixture of acetonitrile and ether and then from ethanol to yield 4-methylamino-3-[3-(5-bromo-3-methylpyrid-2-ylamino)propylamino]-1,2,5-thiadiazole-1-oxide (0.37 g, 25%), m.p. 211°–212° C.

EXAMPLE 7

3-(5-Bromo-3-methylpyrid-2-ylamino)propylamine (1.0 g) was reacted with 3,4-dimethoxy-1,2,5-thiadiazole-1-oxide (0.65 g) in methanol overnight. p-Fluorobenzylamine (0.51 g) was added and the reaction mixture was stirred for 2 hours. The product was filtered off and recrystallised from ethanol to yield 4-(p-fluorobenzylamino)-3-[3-(5-bromo-3-methylpyrid-2-ylamino)propylamino]-1,2,5-thiadiazole-1-oxide (0.77 g, 40%) m.p. 125°–126° C.

EXAMPLE 8

Substituting 3-aminomethylpyridine (5 ml) for methanolic ammonia, using corresponding molar proportions and conditions analogous to those described in Example 1 gave, after chromatography on silica in 10% CH₃OH/CHCl₃ and recrystallisation from propan-2-ol, 3-[3-(5-bromo-3-methylpyrid-2-ylamino)propylamino]-4-(pyrid-3-ylmethylamino)-1,2,5-thiadiazole-1-oxide (0.533 g, 29%), m.p. 162°–165° C.

EXAMPLE 9

3-(5-Bromo-3-methylpyrid-2-ylamino)propylamine (0.7 g) was added dropwise to a stirred solution of 3,4-dimethoxy-1,2,5-thiadiazole-1-oxide (0.46 g) in methanol (20 ml) at room temperature.

After 21 hours, 4-aminomethylpyrimidine (0.37 g) was added and the reaction mixture was stirred for 5 hours. After two days standing, a further addition of 4-aminomethylpyrimidine (0.05 g) was made and the stirred reaction was heated at 30°–50° C. for 3 hours. The reaction mixture was then evaporated in vacuo. The residue (1.4 g) was chromatographed on silica in 10% MeOH/CHCl₃, and then crystallised from ethanol/acetonitrile to give 3-[3-(5-bromo-3-methylpyrid-2-ylamino)-propylamino]-4-(pyrimidin-4-ylmethylamino)-1,2,5-thiadiazole-1-oxide (0.84 g, 65%), m.p. 171°–172° C.

EXAMPLE 10

3-(5-Bromo-3-methylpyrid-2-ylamino)propylamine (0.7 g) was added to a solution of 3,4-dimethoxy-1,2,5-thiadiazole-1-oxide (0.46 g) in methanol (20 ml) at room temperature.

After 3 hours stirring 3-aminomethylpyridine-N-oxide (0.48 g) was added. The reaction mixture was concentrated to ca. 10 ml volume and refluxed for 2 hours and then concentrated in vacuo. The residue (1.6 g) was chromatographed on silica in 20% MeOH/CHCl₃, and then crystallised from methanol to give 3-[3-(5-bromo-3-methylpyrid-2-ylamino)-propylamino]-4-(N-oxopyrid-3-ylmethylamino-1,2,5-thiadiazole-1-oxide (0.36 g, 27%), m.p. 202° C. (decomposition).

EXAMPLE 11

(a) To 4-aminomethylpyridine (15 g) cooled to 0° C. was added, with stirring, acetic anhydride (15 ml). After 30 min., the dark viscous oil was taken up in chloroform and extracted with 5% sodium bicarbonate solution (3×). The aqueous extracts were adjusted to ca. pH 8, saturated with sodium chloride and extracted with chloroform. Concentration afforded 4-pyridylmethylacetamide (9.60 g, 50%) as a yellow solid. To the latter (6.9 g) in dichloromethane (100 ml) was added m-chloroperbenzoic acid (10.2 g) in dichloromethane (50 ml) at 0° C. over 0.5 hr. The mixture was left overnight at room temperature and concentrated. The residue was chromatographed (silica, 10% rising to 25% CH₃OH/CHCl₃) to give pyrid-N-oxo-4-ylmethylacetamide (7.17 g, 93%) as an off-white solid. The latter (5.8 g) was heated under reflux with 95% ethanol (20 ml) and concentrated hydrochloric acid (20 ml) for 1.5 hr. Cooling afforded 4-aminomethylpyridine-N-oxide dihydrochloride (3.85 g, 52%) as a precipitate; m.p. (from ethanol) 176°–178° C.

(b) 3-(5-Bromo-3-methylpyrid-2-ylamino)propylamine (0.7 g) was reacted with 3,4-dimethoxy-1,2,5-thiadiazole-1-oxide (0.46 g) in methanol (20 ml) for 3 hours, followed by the addition of a suspension of 4-aminomethylpyridine N-oxide dihydrochloride (0.75 g) in sodium methoxide (0.16 g sodium in 20 ml methanol). The stirred mixture was concentrated to approximately 10 ml and was then heated under reflux for 5 hours. After cooling overnight the product was filtered off and washed sparingly with methanol, water and again methanol. Recrystallisation from methanol gave 3-[3-(5-bromo-3-methylpyrid-2-ylamino)-propylamino]-4-(N-oxopyrid-4-ylmethylamino)-1,2,5-thiadiazole-1-oxide (0.7 g) m.p. 202° C. (decomposition).

EXAMPLE 12

A pharmaceutical composition for oral administration is prepared containing

| | % by weight |
|---|---|
| 4-Amino-3-[3-(5-bromo-3-methylpyrid-2-ylamino)propylamino]-1,2,5-thiadiazole- | 55 |

-continued

| | | % by weight |
|---|---|---|
| A | 1-oxide | |
| | Dibasic calcium phosphate dihydrate | 20 |
| | Approved coloring agent | 0.5 |
| | Polyvinylpyrrolidone | 4.0 |
| B | Microcrystalline Cellulose | 8.0 |
| | Maize Starch | 8.0 |
| | Sodium glycollate | 4.0 |
| | Magnesium Stearate | 0.5 | by mixing together the ingredients A (substituting lactose or microcrystalline cellulose for dibasic calcium phosphate dihydrate if desired), adding a concentrated solution of polyvinylpyrrolidone and granulating, drying and screening the dried granules; adding the ingredients B to the dried granules and compressing the mixture into tablets containing 5 mg, 25 mg or 50 mg of the free base.

EXAMPLE 13

A pharmaceutical composition for injectable administration is prepared by forming a solution of 4-amino-3-[3-(5-bromo-3-methylpyrid-2-ylamino)propylamino]-1,2,5-thiadiazole-1-oxide in sterile water to give a 1 to 5% w/w solution. The solution is clarified by filtration and filled into vials which are sealed and sterilised. A suitable vial contains 2 ml of the solution.

What is claimed is:

1. A compound of formula (1):

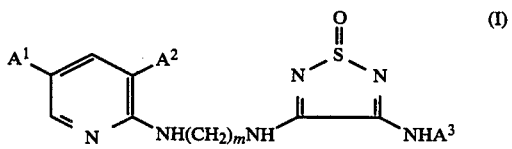

or a pharmaceutically acceptable salt thereof; where
$A^1$ is halogen, nitro, amino, $C_{1-6}$alkyl or $C_{3-4}$alkoxy;
$A^2$ is hydrogen, halogen, nitro, amino, $C_{1-6}$alkyl or $C_{3-4}$alkoxy;
m is 3 or 4;
$A^3$ is hydrogen, $C_{1-6}$alkyl or $CH_2A^4$ where
$A^4$ is phenyl unsubstituted or substituted with one or two substituents which are the same of different and are $C_{1-6}$alkyl, $C_{1-6}$-alkoxy, halogen or hydroxy, or a methylenedioxy group;
or is pyridyl unsubstituted or substituted with one or two substituents which are the same or different and are $C_{1-6}$alkyl, $C_{1-6}$alkoxy, halogen or hydroxy;
or is N-oxopyridyl unsubstituted or substituted with a $C_{1-6}$alkyl, $C_{1-6}$alkoxy, or halogen substituent;
or is pyrimidinyl unsubstituted or substituted with one or two $C_{1-6}$alkyl groups.

2. A compound as claimed in claim 1 where $A^1$ is halogen.

3. A compound as claimed in claim 2 where $A^1$ is bromine.

4. A compound as claimed in claim 1 where $A^2$ is $C_{1-6}$alkyl.

5. A compound as claimed in claim 4 where $A^2$ is methyl.

6. A compound as claimed in claim 1 where $A^3$ is hydrogen.

7. A compound as claimed in claim 1 where $A^4$ is phenyl unsubstituted or substituted with one or two substituents which are the same or different and are $C_{1-6}$alkyl, $C_{1-6}$alkoxy, halogen or hydroxy or a methylenedioxy group.

8. A compound as claimed in claim 7 where $A^4$ is 4-fluorophenyl.

9. A compound as claimed in claim 1 where $A^4$ is pyridyl unsubstituted or substituted with one or two substituents which are the same or different and are $C_{1-6}$alkyl, $C_{1-6}$alkoxy, halogen or hydroxy.

10. A compound as claimed in claim 9 where $A^4$ is pyrid-3-yl.

11. A compound as claimed in claim 1 where $A^4$ is N-oxopyridyl unsubstituted or substituted with a $C_{1-6}$alkyl, $C_{1-6}$alkoxy or halogen substituent.

12. A compound as claimed in claim 11 where $A^4$ is N-oxopyrid-3-yl.

13. A compound as claimed in claim 1 where $A^4$ is a phenyl unsubstituted or substituted with one or two substituents which are the same or different and are $C_{1-6}$alkyl, $C_{1-6}$alkoxy, halogen or hydroxy, or a methylenedioxy group;
or is pyridyl unsubstituted or substituted with one or two substituents which are the same or different and are $C_{1-6}$alkyl, $C_{1-6}$alkoxy, halogen or hydroxy;
or is N-oxopyridyl unsubstituted or substituted with a $C_{1-6}$alkyl, $C_{1-6}$alkoxy, or halogen substituent;
or is pyrimidinyl unsubstituted or substituted with one or two $C_{1-6}$alkyl groups.

14. A compound as claimed in claim 13 where $A^4$ is pyrimidin-4-yl.

15. 3-[4-(5-Bromo-3-methylpyrid-2-ylamino)-butylamino]4-amino-1,2,5-thiadiazole-1-oxide.

16. 3-[3-(5-Bromo-3-methylpyrid-2-ylamino)-propylamino]-4-amino-1,2,5-thiadiazole-1-oxide.

17. 3-[3-(5-Bromo-3-methylpyrid-2-ylamino)-propylamino]-4-methylamino-1,2,5-thiadiazole-1-oxide.

18. 3-[3-(5-Bromo-3-methylpyrid-2-ylamino)-propylamino]-4-(4-fluorobenzylamino-1,2,5-thiadiazole-1-oxide.

19. 3-[3-(5-Bromo-3-methylpyrid-2-ylamino)-propylamino]-4-pyrimid-4-ylmethylamino-1,2,5-thiadiazole-1-oxide.

20. 3-[3-(5-Chloro-3-methylpyrid-2-ylamino)-propylamino]-4-amino-1,2,5-thiadiazole-1-oxide.

21. 3-[3-(3,5-Dibromopyrid-2-ylamino)propylamino]-4-amino-1,2,5-thiadiazole-1-oxide.

22. 3-[3-(5-Bromo-3-methylpyrid-2-ylamino)-propylamino]-4-(pyrid-3-ylmethylamino)-1,2,5-thiadiazole-1-oxide.

23. 3-[3-(5-Bromo-3-methylpyrid-2-ylamino)-propylamino]-4-(N-oxopyrid-3-ylmethylamino)-1,2,5-thiadiazole-1-oxide.

24. 3-[3-(5-Bromopyrid-2-ylamino)propylamino]-4-amino-1,2,5-thiadiazole-1-oxide.

25. 3-[3-(5-Bromo-3-methylpyrid-2-ylamino)-propylamino]-4-(N-oxopyrid-4-ylmethylamino)-1,2,5-thiadiazole-1-oxide.

26. A pharmaceutical composition having histamine $H_1$ antagonist activity, which comprises, in an effective amount to produce such activity, a compound as claimed in claim 1 and a pharmaceutically acceptable carrier.

27. A method of blocking histamine $H_1$-receptors which comprises administering to a subject a non-toxic effective amount to block said receptors of a compound according to claim 1.

* * * * *